United States Patent [19]

Holtkamp, Sr.

[11] Patent Number: Plant 7,254

[45] Date of Patent: Jun. 26, 1990

[54] AFRICAN VIOLET PLANT NAMED IMPROVED NORTH DAKOTA

[76] Inventor: Reinhold Holtkamp, Sr., Blumenstrasse 28, D 4242 Rees-Haffen, Fed. Rep. of Germany

[21] Appl. No.: 362,963

[22] Filed: Jun. 8, 1989

[51] Int. Cl.[5] ..... A01H 5/00

[52] U.S. Cl. ..... Plt./69

[58] Field of Search ..... Plt./69

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A new and distinct cultivar of African violet named Improved North Dakota characterized by its single, violet-shaped, white flowers with purplish blue center and occasionally light purplish blue edges; strong, upright flower stems that curve slightly toward the center to form a compact bouquet above the leaves; medium green, oval to heart-shaped, serrated leaves; profuse flowering, vigorous and compact growth habit, flowering 10–11 weeks after potting, and its long lasting and non-dropping flowers.

1 Drawing Sheet

The present invention comprises a new and distinct cultivar of African violet plant, botanically known as *Saintpaulia ionantha,* and hereinafter referred to by the cultivar name Improved North Dakota.

The new cultivar was referred to during the breeding and selection process by the designation H 50/2 and is a product of a planned breeding program. The basic objective of the breeding program was to create a new African violet cultivar improving certain characteristics of the cultivar North Dakota, disclosed in my U.S. Plant Pat. No. 4,551, granted June, 1980. The new cultivar was originated from a cross made by me in the controlled breeding program in Haffen, Federal Republic of Germany. The female, or seed parent was a cultivar designated C 81/1. The male, or pollen parent was a cultivar designated XIX 4297.

Improved North Dakota was discovered and selected by me as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Improved North Dakota has not been observed under all possible environmental conditions. The phenotype may vary significantly with variations in environment such as temperature, light intensity and day length. The following observations, measurements and values describe the new cultivar as grown in a 10 cm pot in Haffen, West Germany and Nashville, Tenn. under greenhouse conditions which closely approximate those generally used in commercial practice.

The following traits have been repeatedly observed and are determined to be basic characteristics of Improved North Dakota, which in combination distinguish this African violet as a new and distinct cultivar.

(1) Strong, upright flower stems curving slightly toward the center.
(2) Single, violet-shaped white flowers with slightly wavy edges and purplish blue in the center and occasionally on some petal edges.

(3) Each plant carries 7–10 and more upright flower stems each of which carries 7–9 and more flowers.
(4) Long lasting, non-dropping flowers.
(5) Vigorous and compact grower.
(6) Plant saleable 10 to 11 weeks after potting.
(7) Seed capsules push slightly through.
(8) Oval to heart-shaped, serrated, medium green leaves.
(9) After maturity the flowers dry off, and remain on the peduncle without becoming infected by botrytis.

The new cultivar is most similar to, and was specifically intended to improve upon the characteristics of, my previously patented cultivar North Dakota. In comparison to North Dakota, the new cultivar is principally distinguished by its somewhat larger blooms, more compact growth habit, nicer foliage, stronger flowerstems, and by its longer flowering period.

The accompanying color photographic drawing shows a typical specimen plant of the new cultivar. The colors appearing in the photograph are as true as possible with color illustrations of this type.

In the following description, color references are made to The Royal Horticultural Society Color Chart (R.H.S.), except where general colors of ordinary significance are referred to. Color values were taken under natural sunlight conditions at approximately 1 p.m. in Nashville, Tenn.

Botanical classification: *Saintpaulis ionantha,* Ramat., c.v. Improved North Dakota.

Parentage:

*Male parent.*—XIX 4297.

*Female parent.*—C 81/1.

Propagation: The new cultivar holds its distinguishing characteristics through successive propagations by leaf cuttings.

Plant: From 9 cm to 12 cm tall when grown in pots, and approximately 24–28 cm in diameter when fully grown.

*Leaves.*—General form: Oval to heart-shaped. Diameter: 60–70 mm wide, 65–80 mm long. Texture: Soft. Aspect: Serrated, hairy, shiny. Veins: Upperside: well visible; underside: very well pronounced, light green, shiny. Color (upperside): Yellow-Green Group 147 A. Color (underside): Yellow-Green Group 148 D. Petiole: Strong, light green, hairy.

*Flowers.*—Buds: Ball-shaped, 8–9 mm just before opening, greenish white. Sepals: Five (5). Color: Green. Calyx: Shape: Funnel-shaped. Aspect: Spear-shaped, hairy. Peduncle: Character: Strong upright, hairy. Color: Green with brownish touch. Individual flowers: Size: 40 mm to 45 mm. Shape: Single violet-shaped (3 large, 2 small petals). Color (upperside): White with center ranging from Violet Group 88 A to 88 C. Under cooler temperatures and more intensive lighting, the purplish blue tends to intensify. Color (underside): White with center being Violet Group 88 C to D. Borne: Each flower stem carries 7–9 and more flowers on strong, upright peduncle that are free standing above the leaves, thereby forming a compact bouquet. Flowering habit: Flowers 10–11 weeks after potting.

*Reproductive organs.*—Stamens: Two (2). Anthers: 2 composed of 4 anther cells, seed capsule pushes slightly through. Filaments: Yellowish white with purplish blue on edges, 4 mm long. Pollen color: Yellow Group 7 A. Styles: 6–7 mm long, purplish blue, base of ovary light green and hairy.

*Roots.*—Normally developed, white when young, turning slightly brownish when older.

Disease resistance: Good.

General observations: Improved North Dakota is a very attractive, vigorous and compact grower with single violet-shaped, white flowers with purplish blue center and slightly wavy edges. Some metal edges display a fine light purplish blue line. Occasionally, 1–2 additional very small petals develop in the center. A tight bouquet of flowers free standing above leaves develop after approximately 10–11 weeks. Each of the 7–10 and more strong flower stems carries 7–9 and more flowers. The flowers are long-lasting and non-dropping. The medium green, oval to heart-shaped leaves are serrated.

I claim:

1. A new and distinct cultivar of African violet named Improved North Dakota, as described and illustrated, and particularly characterized by its single, violet-shaped, white flowers with purplish blue center and occasionally light purplish blue edges; strong, upright flower stems that curve slightly toward the center to form a compact bouquet above the leaves; medium green, oval to heart-shaped, serrated leaves; profuse flowering, vigorous and compact growth habit, flowering 10–11 weeks after potting, and its long lasting and non-dropping flowers.

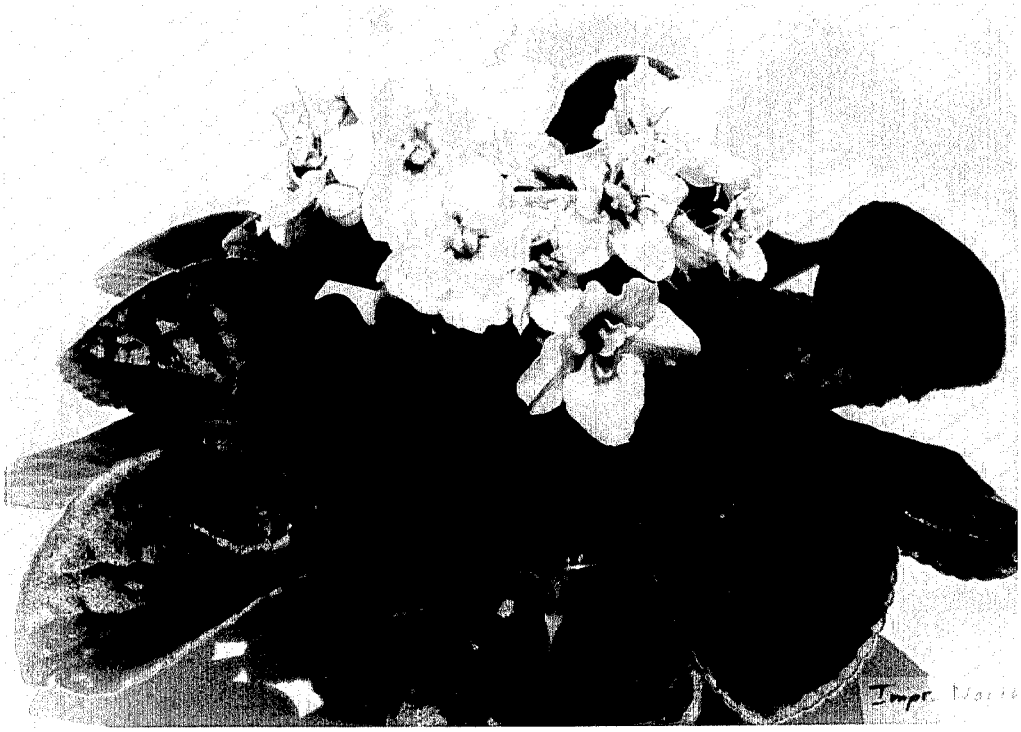

* * * * *